(12) United States Patent
Leem et al.

(10) Patent No.: US 7,981,613 B2
(45) Date of Patent: Jul. 19, 2011

(54) DIAGNOSIS KITS AND METHOD FOR DETECTING CANCER USING POLYMORPHIC MINISATELLITE

(75) Inventors: Sun Hee Leem, Busan (KR); Yun Hee Jeong, Busan (KR); Se Lyun Yoon, Gyeonsangbuk-do (KR); So-Young Seol, Busan (KR)

(73) Assignee: Dong-A University Research Foundation for Industry-Academy Corporation, Busan (KR)

( * ) Notice: Subject to any disclaimer, the term of this patent is extended or adjusted under 35 U.S.C. 154(b) by 0 days.

(21) Appl. No.: 12/302,674

(22) PCT Filed: Jun. 8, 2007

(86) PCT No.: PCT/KR2007/002781
§ 371 (c)(1),
(2), (4) Date: Jun. 18, 2009

(87) PCT Pub. No.: WO2007/142490
PCT Pub. Date: Dec. 13, 2007

(65) Prior Publication Data
US 2009/0269757 A1    Oct. 29, 2009

(30) Foreign Application Priority Data
Jun. 9, 2006 (KR) ........................ 10-2006-0051901

(51) Int. Cl.
*C12Q 1/68* (2006.01)
(52) U.S. Cl. .................... 435/6; 435/91.1; 536/24.33
(58) Field of Classification Search .................. None
See application file for complete search history.

(56) References Cited

U.S. PATENT DOCUMENTS
6,576,423 B2    6/2003   Batra et al.
6,812,339 B1 *  11/2004  Venter et al. ............. 536/24.31
2005/0130172 A1 *  6/2005  Beard et al. ........................ 435/6

FOREIGN PATENT DOCUMENTS
JP    10-262678 A    10/1998
KR    1020030058023 A    7/2003

OTHER PUBLICATIONS

Toribara et al. J. Clin. Invest. vol. 88:1005-1013. 1991.*
The Stratagene Catalog p. 39. 1988.*
Vinall, Lynne E. et al., Polymorphism of Human Mucin Genes in Chest Disease, American Journal of Respiratory Cell and Molecular Biology, 2000, pp. 678-686, vol. 23(5).
Gum, James R. et al., Identification and characterization of the MUC2 (human intestinal mucin) gene 5'-flanking region: promoter activity in cultured cells, The Biochemical Journal, 1997, pp. 259-267, vol. 325(1).

* cited by examiner

*Primary Examiner* — Heather Calamita
(74) *Attorney, Agent, or Firm* — Tristan A. Fuierer; Moore & Van Allen, PLLC

(57) ABSTRACT

The present invention relates to a kit and a method for diagnosing cancer using polymorphic minisatellites (MS), more specifically, relates to a primer set for detecting polymorphic minisatellites MUC2-MS6 or MUC2-MS7 in the MUC2 gene, a DNA typing kit comprising said primer set, and a kit and a method for diagnosing cancer using a primer set for detecting polymorphic minisatellites MUC2-MS6, MUC2-MS7 or hTERT-VNTR 2-2. According to the present invention, DNA typing of MUC2-MS6 and MUC2-MS7 can effectively achieve the parentage identification, kinship identification or medicolegal examination, because the polymorphic minisatellites MUC2-MS6 and MUC2-MS7 are inherited through meiosis according to Mendelian genetics. In addition, the polymorphic minisatellites MUC2-MS6, MUC2-MS7 and hTERT-VNTR 2-2 can be used to predict and diagnose various cancers; such as gastric cancer, colon cancer, rectal cancer and prostate cancer etc.

9 Claims, 6 Drawing Sheets

GF: grand father, GM: grand mother
F: father M: mother
1,2,3: off springs

SEQUENCE LISTING

<160> NUMBER OF SEQ ID NOS: 36

<210> SEQ ID NO 1
<211> LENGTH: 36
<212> TYPE: DNA
<213> ORGANISM: Artificial Sequence
<220> FEATURE:
<223> OTHER INFORMATION: Synthetic Construct

<400> SEQUENCE: 1
gggtagaggc cctcaggcat gggctggcgg gtgggt     36

<210> SEQ ID NO 2
<211> LENGTH: 34
<212> TYPE: DNA
<213> ORGANISM: Artificial Sequence
<220> FEATURE:

<223> OTHER INFORMATION: Synthetic Construct

<400> SEQUENCE: 2
gccgggcacc gggagctggg gggacactca ccgt                         34

<210> SEQ ID NO 3
<211> LENGTH: 12
<212> TYPE: DNA
<213> ORGANISM: Artificial Sequence
<220> FEATURE:
<223> OTHER INFORMATION: Synthetic Construct

<400> SEQUENCE: 3
ctcctctggg tc                                                 12

<210> SEQ ID NO 4
<211> LENGTH: 60
<212> TYPE: DNA
<213> ORGANISM: Artificial Sequence
<220> FEATURE:
<223> OTHER INFORMATION: Synthetic Construct

<400> SEQUENCE: 4
gcagagcagg gctgtaggtg ggctatagct gtgggcgggg ccatgggcgg ggccgactaa     60

<210> SEQ ID NO 5
<211> LENGTH: 54
<212> TYPE: DNA
<213> ORGANISM: Artificial Sequence
<220> FEATURE:
<223> OTHER INFORMATION: Synthetic Construct

<400> SEQUENCE: 5
cacacagtca cacatgcaca catgcataga cacagacaca caggcacaca cagt           54

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
caccactccc agccctccac caac                                    24

<210> SEQ ID NO 7
<211> LENGTH: 46
<212> TYPE: DNA
<213> ORGANISM: Artificial Sequence
<220> FEATURE:
<223> OTHER INFORMATION: Synthetic Construct

<400> SEQUENCE: 7
ccacccaccc acctatccat ccatccatcc accatctatc taccat            46

<210> SEQ ID NO 8
<211> LENGTH: 86
<212> TYPE: DNA
<213> ORGANISM: Artificial Sequence
<220> FEATURE:
<223> OTHER INFORMATION: Synthetic Construct

<400> SEQUENCE: 8
cctgtgcagt ggccccgggg gcttggcctg ggaggagcca ccctcacggg ccgcgtgcac     60
accctgtctt cagagtgcaa caccag                                  86

```
<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cccttcccca tccccagcta                                                  20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ggcactcacc ccagcctctg                                                  20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gaccccacgc tggtgctttc                                                  20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ccccgaagtg caccgagaag                                                  20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ggcctttcct cagccccaga                                                  20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ggctggtgca cccaccttgt                                                  20

<210> SEQ ID NO 15
<211> LENGTH: 23
<212> TYPE: DNA
<213> ORGANISM: Artificial Sequence
<220> FEATURE:
<223> OTHER INFORMATION: Primer
```

-continued

```
<400> SEQUENCE: 15
tgttcagcat ctgccacagc aag                                        23

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
tagcatgctc tacggcaccc tca                                        23

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
tgcatggaca ctgacacgca ag                                         22

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gcaggggcga ggagaggaag                                            20

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
tgttgctggc ccatggataa gtgt                                       24

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
aggggttgtc gttgagaatg gtga                                       24

<210> SEQ ID NO 21
<211> LENGTH: 17
<212> TYPE: DNA
<213> ORGANISM: Artificial Sequence
<220> FEATURE:
<223> OTHER INFORMATION: Primer

<400> SEQUENCE: 21
gtaggcccca ccgtgtt                                               17

<210> SEQ ID NO 22
<211> LENGTH: 27
<212> TYPE: DNA
```

```
<213> ORGANISM: Artificial Sequence
<220> FEATURE:
<223> OTHER INFORMATION: Primer

<400> SEQUENCE: 22
tagaagctct gacatgacat cttggcc                                            27

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
cctctgctgt gccccttgag ag                                                 22

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
accttccagg caccatcttg ctc                                                23

<210> SEQ ID NO 25
<211> LENGTH: 42
<212> TYPE: DNA
<213> ORGANISM: Artificial Sequence
<220> FEATURE:
<223> OTHER INFORMATION: Synthetic Construct

<400> SEQUENCE: 25
gagtgaggcg tggtccccgg gtgtccctgt cacgtgcagg gt                            42

<210> SEQ ID NO 26
<211> LENGTH: 61
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n = c or t
<220> FEATURE:
<221> NAME/KEY: misc_feature
<222> LOCATION: (2)..(2)
<223> OTHER INFORMATION: n = g or t
<220> FEATURE:
<221> NAME/KEY: misc_feature
<222> LOCATION: (17)..(17)
<223> OTHER INFORMATION: n = c or t
<220> FEATURE:
<221> NAME/KEY: misc_feature
<222> LOCATION: (24)..(24)
<223> OTHER INFORMATION: n = c or t
<220> FEATURE:
<221> NAME/KEY: misc_feature
<222> LOCATION: (39)..(39)
<223> OTHER INFORMATION: n = c or t

<400> SEQUENCE: 26
nngtgagctg gatgtgnggt gtcnggatgg tgcaggtcng ggtgaggtc gccaggccct         60
g                                                                        61

<210> SEQ ID NO 27
```

```
<211> LENGTH: 38
<212> TYPE: DNA
<213> ORGANISM: Artificial Sequence
<220> FEATURE:
<223> OTHER INFORMATION: Synthetic Construct

<400> SEQUENCE: 27
gtgggattgg ttttcatgtg cggggtaggt ggggatct                                38

<210> SEQ ID NO 28
<211> LENGTH: 36
<212> TYPE: DNA
<213> ORGANISM: Artificial Sequence
<220> FEATURE:
<223> OTHER INFORMATION: Synthetic Construct

<400> SEQUENCE: 28
ggggtctgat gtgtggtgac tgtggatggc ggtcgt                                  36

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gctgcgtctt gcgtgactgg                                                    20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tacccaggca atgggcaacc                                                    20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tgggagcatc actcacagga                                                    20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ggaacacagc caaccccatta                                                   20

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
```

```
gtgacgttgc ttctgtgcct cctt                                      24

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
cgaccccaga gtggaagaaa caga                                      24

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
actcttctcc tgcctgtgct gtgg                                      24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
gtttcttccg atcaggacgt gtgg                                      24
```

DIAGNOSIS KITS AND METHOD FOR DETECTING CANCER USING POLYMORPHIC MINISATELLITE

CROSS-REFERENCE TO RELATED APPLICATIONS

This application is filed under the provisions of 35 U.S.C. §371 and claims the priority of International Patent Application No. PCT/KR2007/002781 filed on 8 Jun. 2007 entitled "Diagnosis Kits and Method for Detecting Cancer Using Polymorphic Minisatellite" in the name of Sun Hee Leem, et al., which claims priority of Korean Patent Application No. 10-2006-0051901 filed on 9 Jun. 2006, both of which are hereby incorporated by reference herein in their entirety.

TECHNICAL FIELD

The present invention relates to a kit and a method for diagnosing cancer using polymorphic minisatellites (MS), and more particularly to a primer set for detecting polymorphic minisatellites MUC2-MS6 or MUC2-MS7 in the MUC2 gene, a DNA typing kit comprising the primer set, and a kit and a method for diagnosing cancer using a primer set for detecting polymorphic minisatellites MUC2-MS6, MUC2-MS7 or hTERT-VNTR 2-2.

BACKGROUND ART

Mucin is a major component of mucus, which functions to secrete mucus to the epithelial cells of the digestive system, and respiratory organs such as the airway. Thus, it functions to protect the intestinal surface, which is epithelial tissue, from the mechanical damage and chemical stimulation of each organ and acts as a lubricant for a bowel movement. 20 mucin genes performing such functions have been identified to date and can be broadly divided, according to function, into secretory mucins (MUC2, MUC5AC, MUC5B, MUC6, MUC7, MUC9 and MUC19) and membrane-bound mucins (MUC1, MUC3A, MUC3B, MUC4, MUC12, MUC17, MUC18 and MUC20). The membrane-bound mucins are involved in the secretion and migration of the secretory mucins.

Among such mucin genes, the secretory mucins MUC2, MUC5AC, MUC5B and MUC6 genes are clustered on human chromosome 11p15.5 to form a gene cluster (FIG. 1). Also, such structural characteristics were also found in mouse genomes.

This indicates that the structural characteristics of a cluster of genes having the same function are highly conserved in other species, and the group of the secretory mucin genes is considered to have a close connection with the relative expression and function of genes.

When the secretory mucin genes are in a normal state, they will secrete mucus from different organs to protect each organ and the intestines, but when they are regulated or have abnormality, they will excessively secrete mucus. It has been reported that, in the case of bronchi, such excessive secretion causes asthma or involves inflammatory disease, and in the case of gastric cancer, excessive mucus increases tolerance to various pathogenic bacteria, thus increasing the incidence of tumors such as gastric cancer.

Also, the secretory mucins were observed to commonly have tandem repeats (TRs) in the central region of the genes. It was reported that, due to such TR structures, the mucosal characteristics of mucin appear, and structural mutations in the TR regions are attributable to genetic diseases found in human beings. These mucin genes having highly complex structural characteristics are not yet completely separated in the genome, but the base sequences thereof are gradually being identified as a result of the human genome project.

Many recent studies revealed that such tandem repeat (TR) sequences take up more than 10% of the human genome, cause many diseases and are very important factors in the regulation and evolution of gene expression. The TR sequences are divided, according to length thereof, into monomorphic sequences having only a single length in all individuals, and polymorphic sequences, which have more than 2 alleles and vary depending on individuals. The polymorphic repeat sequences have important meaning as genomic markers which can be used in human genome mapping in initial genomics studies. Thus, the analysis of TRs and polymorphisms in the structurally highly complex mucin genes allows studies on the correlation of the genes with diseases.

Meanwhile, telomerase is a ribonucleoprotein complex consisting of active subunit TERT (human telomerase reverse transcriptase) and TR (telomerase RNA) as a RNA component that provides a template for the synthesis of telomeric DNA. Telomerase is expressed mainly in germ cells and stem cells as reproductive cells of adult somatic cells, but is not expressed in other somatic cells, and thus the length of the telomere region is gradually shortened with an increase in cell division rate. When telomeres are significantly shortened, DNA damage checkpoint will be activated, cell division will be stopped, and cell aging will be induced. Thus, the activation of telomerase appears in most tumor cells where cell aging does not occur.

The RNA component of telomerase is expressed in most embryonic and adult tissues, but the expression of TERT correlates directly with the activity of telomerase. The 5'-promoter region of human gene hTERT encoding TERT includes binding sites of various transcription factors regulating expression, and various forms of hTERT transcripts were detected. These results indicate that the expression of telomerase can be regulated by transcriptional mechanisms and/or post-transcriptional mechanisms such as selective splicing.

The present inventors have made many efforts to develop a kit and a method for diagnosing cancer using polymorphic minisatellites and, as a result, found that the minisatellites (MS) of secretory mucin gene MUC2 are inherited through meiosis according to Mendelian genetics, and polymorphic minisatellites MUC2-MS6, MUC2-MS7 and hTERT-VNTR 2-2 are related to the development of tumors such as gastric cancer, colon cancer, rectal cancer and prostate cancer, thereby completing the present invention.

SUMMARY OF THE INVENTION

It is a main object of the present invention to provide a polymorphic minisatellite for predicting and diagnosing a tumor.

Another object of the present invention is to provide a primer set for detecting said polymorphic minisatellite.

Still another object of the present invention is to provide a DNA typing kit comprising said primer set.

Yet another object of the present invention is to provide a kit and a method for diagnosing cancer using said primer set.

To achieve the above objects, in one aspect, the present invention provides a polymorphic minisatellite for predicting and diagnosing a tumor selected from the group consisting of gastric cancer, colon cancer and rectal cancer, the polymorphic minisatellite having a base sequence of SEQ ID NO: 6 (MUC2-minisatellite6, MUC2-MS6) or SEQ ID NO: 7 (MUC2-minisatellite7, MUC2-MS7).

In another aspect, the present invention provides a set of primers for detecting a polymorphic minisatellite of SEQ ID NO: 6 (MUC2-MS6), the primers having base sequences of SEQ ID NO: 19 and SEQ ID NO: 20, respectively.

In still another aspect, the present invention provides a set of primers for detecting a polymorphic minisatellite of SEQ ID NO: 7 (MUC2-MS7), the primers having base sequences of SEQ ID NO: 21 and SEQ ID NO: 22, respectively.

In yet another aspect, the present invention provides a DNA typing kit for detecting a polymorphic minisatellite of SEQ ID NO: 6 (MUC2-MS6) or a polymorphic minisatellite of SEQ ID NO: 7 (MUC2-MS7), the DNA typing kit comprising said primer set.

In yet still another aspect, the present invention provides a kit for diagnosing a tumor selected from the group consisting of gastric cancer, colon cancer and rectal cancer, the kit comprising said primer set, DNA polymerase and dNTPs (dGTP, dCTP, dATP and dTTP).

In still further another aspect, the present invention provides a polymorphic minisatellite hTERT-VNTR (human telomerase reverse transcriptase-variable number of tandem repeats) 2-2 for predicting and diagnosing prostate cancer, the polymorphic minisatellite hTERT-VNTR 2-2 having a base sequence of SEQ ID NO: 26.

In still further another aspect, the present invention provides a kit for diagnosing prostate cancer, the kit comprising a set of primers for detecting polymorphic minisatellite hTERT-VNTR 2-2, DNA polymerase and dNTPs (dGTP, dCTP, dATP and dTTP), the primers having base sequences of SEQ ID NO: 31 and SEQ ID NO: 32, respectively.

In yet further another aspect, the present invention provides a method for diagnosing a cancer selected from the group consisting of gastric cancer, colon cancer, prostate cancer and rectal cancer, the method comprising the steps of: (a) performing PCR using the genomic DNA of a sample as a template, and at least one primer set selected from the group consisting of a set of primers of SEQ ID NOs: 19 and 20, a set of primers of SEQ ID NOs: 21 and 22, and a set of primers of SEQ ID NOs: 31 and 32; and (b) determining the rearrangement of polymorphisms of MUC2-MS6, MUC2-MS7 and hTERT-VNTR 2-2, on the basis of the PCR product.

Another features and embodiments of the present invention will be more clarified from the following "detailed description" and the appended "claims".

BRIEF DESCRIPTION OF DRAWINGS

FIG. 1(A) shows the band structure of chromosome 11, analyzed using the MAP Viewer of the NCBI website, and FIG. 1(B) depicts mucin genes on chromosome 11p15.5, in which MUC2, MUC5AC and MUC5B are oriented toward the centromere, whereas MUC6 is oriented toward the telomere.

In FIG. 2, an exon is indicated by a black color, and the locations of minisatellites detected by the Tandem Repeats Finder Program are indicated by a star symbol (*).

In FIG. 5, first and last lanes indicate size markers. GF and GM represent a grandfather and a grandmother, respectively, F and M represent a father and a mother, respectively, and the DNA samples of offspring is indicated by 1, 2 and 3.

In FIG. 8, the tumor tissue sample of gastric cancer is indicated by a star symbol, M represents a size marker, and rearrangement in tumor tissue is indicated by an arrow.

FIG. 9A shows the polymorphic pattern of hTERT-VNTR 2-2 in normal persons, and FIG. 9B shows the polymorphic pattern of hTERT-VNTR 2-2 in prostate cancer patients.

DETAILED DESCRIPTION OF THE INVENTION, AND PREFERRED EMBODIMENTS

Figure 1:
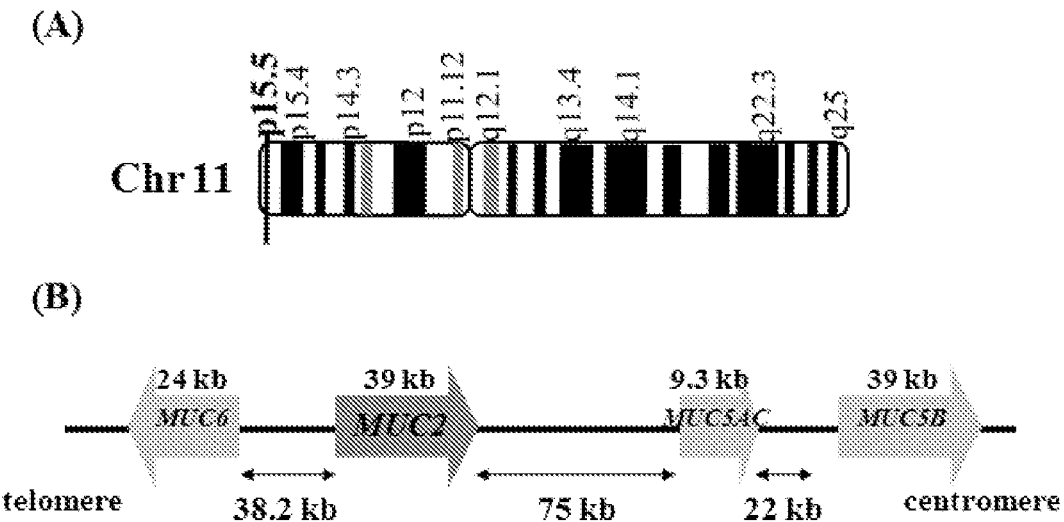
FIG. 1 is a schematic diagram showing the locations and orientations of mucin genes located at the distal end of human chromosome 11. Specifically.

In one aspect, the present invention relates to a polymorphic minisatellite for predicting and diagnosing tumors, which has a base sequence of SEQ ID NO: 6 (MUC2-MS6) or SEQ ID NO: 7 (MUC2-MS7).

In another aspect, the present invention relates to a primer set for detecting a polymorphic minisatellite of SEQ ID NO: 6 (MUC2-MS6) or a polymorphic minisatellite of SEQ ID NO: 7 (MUC2-MS7).

According to the present invention, the structural characteristics of the MUC2 (NC_000011 REGION: 1064902 . . . 1094413) gene were analyzed using BLAST and, as a result, it was found that the gene includes 8 tandem repeats (TR).

The polymorphisms of 8 minisatellites present in the MUC2 gene were analyzed by PCR and, as a result, MUC2-MS5 and MUC2-MS8 could not be used as individual identification markers because they showed monomorphism, and MUC2-MS1, MUC2-MS2, MUC2-MS3, MUC2-MS4, MUC2-MS6 and MUC2-MS7 all showed polymorphism. In particular, MUC2-MS6 located in the exon showed polymorphism, and the minisatellite region, which exists in the exon region and shows polymorphism, is not known in the prior art. The fact that the exon region is polymorphic means that the number of secreted proteins varies depending on individuals, indicating that the size of mucous substances of mucins varies depending on individuals.

In another aspect, the present invention relates to a DNA typing kit for detecting a polymorphic minisatellite of SEQ ID NO: 6 (MUC2-MS6) or a polymorphic minisatellite SEQ ID NO: (MUC2-MS7), the DNA typing kit comprising said primer set.

Alleles in the tandem repeat regions consist of two alleles inherited from parents. According to the present invention, in order to determine whether the alleles are inherited to offspring through meiosis, genomic DNA was extracted from the blood of each of grandparents, parents and offspring and subjected to PCR to analyze the allele patterns of MUC2-MS1, MUC2-MS3, MUC2-MS4, MUC2-MS6 and MUC2-MS7. As a result, MUC2-MS1, MUC2-MS3, MUC2-MS4, MUC2-MS6 and MUC2-MS7 were all inherited from parents to offspring. This suggests that minisatellites in the genes can be used as individual identification markers and can be used to predict whether the same disease occurs in the same family.

In still another aspect, the present invention relates to a kit for diagnosing a cancer selected from the group consisting of gastric cancer, colon cancer and rectal cancer, the kit comprising said primer set.

In the diagnostic kit according to the present invention, the rearrangement of polymorphic MUC2-MS6 and MUC2-MS7 is determined by performing PCR using, as a template, genomic DNA isolated from the tissue of a sample, and DNA polymerase is preferably taq polymerase suitable for PCR.

In order to examine the effect of the tandem repeat (TR) regions on the expression of the MUC2 gene, the genomic DNA of each of normal persons and gastric cancer patients was extracted and subjected to PCR to compare haplotype patterns between the normal patient and the gastric cancer patient. As a result, the MUC2-MS1, MUC2-MS3 and MUC2-MS4 regions did not show a gastric cancer-specific allele, whereas the MUC2-MS6 and MUC2-MS7 regions showed gastric cancer-specific alleles. This suggests that MUC2-MS6 and MUC2-MS7 can be used as markers for predicting and diagnosing gastric cancer.

The frequencies of rare alleles of MUC2-MS6 and MUC2-MS7 in normal persons and tumor patients were measured. As a result, the frequency of rare alleles of MUC2-MS6 was higher in gastric cancer patients, and the frequency of rare alleles of MUC2-MS7 was higher in rectal cancer patients. This suggests that the rare alleles of MUC2-MS6 are related to gastric cancer, and the rare alleles of MUC2-MS7 are related to rectal cancer.

Also, the risk of tumor development was measured. As a result, in the case of having at least one rare allele of MUC2-MS6, the risk of gastric cancer and the risk of colon cancer were relatively high, and in the case of having at least one rare allele of MUC2-MS7, the risk of rectal cancer development was relatively high. This suggests that the rare alleles of MUC2-MS6 are not related to colon cancer, but rather are related to gastric cancer and colon cancer, and the rare alleles of MUC2-MS7 are related to rectal cancer.

The frequencies of rare alleles of MUC2-MS6 and MUC2-MS7 according to age were measured. As a result, as age decreased, the frequency of rare alleles of MUC2-MS6 in gastric cancer patients and colon cancer patients was increased, and the frequency of rare alleles of MUC2-MS7 was higher in rectal cancer patients. This suggests that, as age decreases, the correlation of the rare alleles of MUC2-MS6 with gastric cancer and colon cancer is increased, and the correlation of the rare alleles of MUC2-MS7 with rectal cancer is increased.

In yet another aspect, the present invention relates to polymorphic minisatellite hTERT-VNTR 2-2 for predicting and diagnosing prostate cancer and to a kit for diagnosing prostate cancer, the kit comprising a primer set for detecting the hTERT-VNTR 2-2.

The present inventors previously found that a human telomerase (hTERT) gene includes four minisatellites (VNTR 2-1, VNTR 2-2, VNTR 6-1 and VNTR 6-2), and the polymorphic minisatellites are passed on to offspring through meiosis and can be used to diagnose telomerase-related diseases, including rectal cancer, testicular cancer, skin cancer, gastric cancer and renal cancer (Korean Patent Registration No. 10-0431285).

In the present invention, in order to confirm whether hTERT-VNTR 2-2 is useful for the diagnosis of prostate cancer, the frequency of rare alleles of hTERT-VNTR 2-2 was examined. As a result, the frequency of rare alleles of hTERT-VNTR 2-2 was higher in prostate cancer patients, and in the case of having the rare alleles of hTERT-VNTR 2-2, the risk of prostate cancer development was increased. This suggests that hTERT-VNTR 2-2 can be used as a marker capable of predicting and diagnosing prostate cancer.

In yet still another aspect, the present invention relates to a method for diagnosing a cancer selected from the group consisting of gastric cancer, colon cancer, rectal cancer and prostate cancer, the method comprising the steps of: (a) performing PCR using the genomic DNA of a sample as a template, and at least one primer set selected from a set of primers of SEQ ID NOs: 19 and 20, a set of primers of SEQ ID NOs: 21 and 22, and a set of primers of SEQ ID NOs: 31 and 32; and (b) determining the rearrangement of polymorphisms of MUC2-MS6, MUC2-MS7 and hTERT-VNTR 2-2, on the basis of the PCR products.

In the diagnostic method of the present invention, the rearrangement of the polymorphisms of MUC2-MS6, MUC2-MS7 and hTERT-VNTR 2-2 is preferably a deletion of one allele or loss of heterozygosity. This rearrangement can be confirmed by comparing electrophoresis photographs of polymorphic minisatellites MUC2-MS6, MUC2-MS7 and hTERT-VNTR 2-2 between cancer tissue and normal tissue. As a result, MUC2-MS6, MUC2-MS7 and hTERT-VNTR 2-2 showed rearrangement patterns in cancer tissue, which were different from normal tissue. This suggests that cancers, including gastric cancer, colon cancer, rectal cancer and prostate cancer, can be diagnosed by determining whether the polymorphisms of MUC2-MS6, MUC2-MS7 and hTERT-VNTR 2-2 have rearrangements.

EXAMPLES

Hereinafter, the present invention will be described in further detail with reference to examples. It will be apparent to those skilled in the art that the scope of the present invention is not limited by these examples, and various modifications and alternations are possible, without departing from the sprit and scope of the present invention.

Example 1

Figure 2:
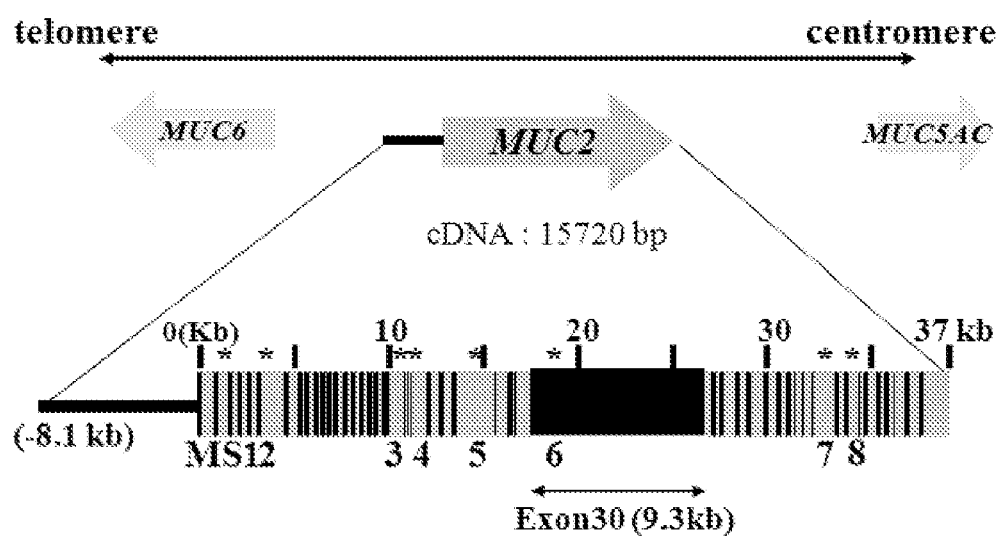
FIG. 2 is a schematic diagram showing the structure of the MUC2 gene and the position of minisatellites (MS) in the gene.

Analysis of Structural Characteristics of MUC2 Gene and Analysis of Polymorphisms of Minisatellites (MS) in MUC2 Gene The structural characteristics of the MUC2 (NC_000011 REGION: 1064902 . . . 1094413) gene were analyzed using BLAST. Specifically, the exon and intron regions present in the open reading frame were examined, the locations of tandem repeats (TR) in each of the regions were determined, and then the locations of minisatellites (MS) having a repeat sequence of about 10-100 bp were analyzed. As a result, the MUC2 gene consisted of 48 exons having a size of about 40 kb and we analyzed the 8 TR regions in the gene (see Table 1 and FIG. 2).

The polymorphisms of 8 minisatellites (MS) (Table 1) present in the MUC2 gene were analyzed by PCR. The base sequences of primers used in the PCR analysis are shown in Table 2 below.

TABLE 1

Tandem repeats (TR) present in MUC2 gene

| Mini-satellite (MS) | Indices | Position | Size of most common allele (bp) | Repeat size | Copy no. in most common allele |
|---|---|---|---|---|---|
| MUC2-MS1 | 1566-2168 | Intron 2 | 602 (796) | 38 | 16.7 |
| MUC2-MS2 | 3881-4694 | Intron 6 | 813 (897) | 34 | 24.9 |
| MUC2-MS3 | 10213-10573 | Intron 20 | 360 (493) | 12 | 26.9 |
| MUC2-MS4 | 11645-11958 | Intron 23 | 313 (413) | 60 | 5.2 |
| MUC2-MS5 | 14627-15192 | Intron 26 | 566 (693) | 54 | 10.4 |
| MUC2-MS6 | 17495-18977 | Exon 30 | 1482 (1577) | 24 | 62.7 |
| MUC2-MS7 | 32674-32953 | Intron 41 | 280 (871) | 46 | 6.1 |
| MUC2-MS8 | 34017-34194 | Intron 42 | 178 (359) | 85 | 2 |

| Polymorphism | Consensus sequence | GC content (%) | SEQ ID NO: |
|---|---|---|---|
| MUC2-MS1 | GGGTAGAGGCCCTCAGGCATGGGCTGGCGGGTGGGT | 38 | 1 |
| MUC2-MS2 | GCCGGGCACCGGGAGCTGGGGGGACACTCACCGT | 72 | 2 |
| MUC2-MS3 | CTCCTCTGGGTC | 12 | 3 |
| MUC2-MS4 | GCAGAGCAGGGCTGTAGGTGGGCTATAGCTGTGGGCGGGGCCATGGGCGGGGCCGACTAA | 67 | 4 |
| MUC2-MS5 | CACACAGTCACACATGCACACATGCATAGACACAGACACACAGGCACACACAGT | 49 | 5 |
| MUC2-MS6 | CACCACTCCCAGCCCTCCACCAAC | 61 | 6 |
| MUC2-MS7 | CCACCCACCCACCTATCCATCCATCCATCCACCATCTATCTACCAT | 54 | 7 |
| MUC2-MS8 | CCTGTGCAGTGGCCCCGGGGGCTTGGCCTGGGAGGAGCCACCCTCACGGGCCGCGTGCACACCCTGTCTTCAGAGTGCAACACCAG | 85 | 8 |

TABLE 2

Primers used for detection of polymorphisms

| Polymorphisms | Primer | Amino acid sequence | SEQ ID NO: |
|---|---|---|---|
| MUC2-MS1 | MUC2-MS1 F | CCCTTCCCCATCCCCAGCTA | 9 |
| | MUC2-MS1 R | GGCACTCACCCCAGCCTCTG | 10 |
| MUC2-MS2 | MUC2-MS2 F | GACCCCACGCTGGTGCTTTC | 11 |
| | MUC2-MS2 R | CCCCGAAGTGCACCGAGAAG | 12 |
| MUC2-MS3 | MUC2-MS3 F | GGCCTTTCCTCAGCCCCAGA | 13 |
| | MUC2-MS3 R | GGCTGGTGCACCCACCTTGT | 14 |
| MUC2-MS4 | MUC2-MS4 F | TGTTCAGCATCTGCCACAGCAAG | 15 |
| | MUC2-MS4 R | TAGCATGCTCTACGGCACCCTCA | 16 |
| MUC2-MS5 | MUC2-MS5 F | TGCATGGACACTGACACGCAAG | 17 |
| | MUC2-MS5 R | GCAGGGGCGAGGAGAGGAAG | 18 |
| MUC2-MS6 | MUC2-MS6 F | TGTTGCTGGCCCATGGATAAGTGT | 19 |
| | MUC2-MS6 R | AGGGGTTGTCGTTGAGAATGGTGA | 20 |
| MUC2-MS7 | MUC2-MS7 F | GTAGGCCCCACCGTGTT | 21 |
| | MUC2-MS7 R | TAGAAGCTCTGACATGACATCTTGGCC | 22 |
| MUC2-MS8 | MUC2-MS8 F | CCTCTGCTGTGCCCCTTGAGAG | 23 |
| | MUC2-MS8 R | ACCTTCCAGGCACCATCTTGCTC | 24 |

Among 8 TR regions present in the MUC2 gene, the allele patterns of the MS5 (minisatellite5) region located in intron 26 and the MS8 region located in intron 42 were compared by PCR using genomic DNA extracted from the blood of 100 adult men and women.

For this purpose, genomic DNA was amplified under standard PCR conditions (50 mM Tris-HCl (pH 9.0), 50 mM $MgCl_2$, 0.2 mM dTTP, 0.2 mM dCTP, 0.2 mM dGTP, 0.2 mM dATP, 50 µL of final volume) with primers of SEQ ID NOs: 17 and 18 for MS5 and primers of SEQ ID NOs: 23 and 24 for MS8. The PCR analysis of the DNA samples was performed using, as a template, 100 ng of genomic DNA, with Promega GoTaq Flexi DNA polymerase (Promega). The PCR reactions were performed in the following conditions: for MS5, annealing at 94° C. for 2 minutes, and then 30 cycles of 45 sec at 94° C. and 1 min at 68° C., followed by final extension at 68° C. for 7 min; and for MS8, annealing at 94° C. for 2 min, and then 30 cycles of 45 sec at 94° C., 30 sec at 62° C. and 20 sec at 72° C., followed by final extension at 72° C. for 7 min. The PCR products were added to 1% SeaKem LE agarose gel, and then analyzed by electrophoresis (1 volt/cm) in TAE buffer. As a result, MUC2-MS5 and MUC2-MS8 could not be used as individual identification markers because they showed monomorphism.

Among 8 TR regions present in the MUC2 gene, the allele patterns of MS1 located in intron 2, MS2 located in intron 6, MS3 located in intron 20, MS4 located in intron 23, MS6 located in exon 30 and MS7 located in intron 41 were compared by PCR using genomic DNA extracted from the blood of 100 adult men and women.

For this purpose, genomic DNA was amplified under standard PCR conditions (50 mM Tris-HCl (pH 9.0), 50 mM $MgCl_2$, 0.2 mM dTTP, 0.2 mM dCTP, 0.2 mM dGTP, 0.2 mM dATP, 50 μL of final volume) with primers of SEQ ID NOs: 9 and 10 for MS1, primers of SEQ ID NOs: 11 and 12 for MS2, primers of SEQ ID NOs: 13 and 14 for MS3, primers of SEQ ID NOs: 15 and 16 for MS4, primers of SEQ ID NOs: 19 and 20 for MS6, and primers of SEQ ID NOs: 21 and 22 for MS7. The PCR analysis of the DNA samples was performed using, as a template, 100 ng of genomic DNA, with Promega GoTaq Flexi DNA polymerase (Promega). The PCR reactions were performed in the following conditions: for MS1, annealing at 94° C. for 2 min, and then 30 cycles of 45 sec at 94° C., 30 sec at 62° C. and 1 min at 72° C., followed by final extension at 72° C. for 7 min; for MS2, annealing at 94° C. for 2 min, and then 30 cycles of 45 sec at 94° C., 30 sec at 62° C. and 2 min at 72° C., followed by final extension at 72° C. for 7 min; for MS3, annealing at 94° C. for 2 min, and then 25 cycles of 45 sec at 94° C. and 2 min at 69° C., followed by final extension at 72° C. for 7 min; for MS4, annealing at 94° C. for 2 min, and then 30 cycles of 45 sec at 94° C. and 1 min at 68° C., followed by final extension at 68° C. for 7 min; for MS6, annealing at 94° C. for 2 min, and then 30 cycles of 45 sec at 94° C. and 1 min at 68° C., followed by final extension at 72° C. for 7 min; and for MS7, annealing at 94° C. for 2 min, 30 cycles of 45 sec at 94° C. and 2 min at 69° C., followed by final extension at 72° C. for 7 min. The PCR products were added to 2% SeaKem LE agarose gel for MS1, MS4 and MS7, 1% SeaKem LE agarose gel for MS2 and MS6, and 3% Metaphor gel for MS3, and then analyzed by electrophoresis (1 volt/cm) in TAE buffer. As a result, the products all showed polymorphism, and thus additional analysis was performed using increased number of individuals. Herein, N is the number of alleles and corresponds to two times the number of samples because every individual has two alleles.

(1) MUC2-MS1 (Minisatellite 1)

400 normal persons were examined and, as a result, three alleles having sizes of 644 bp, 758 bp and 796 bp were found, which consisted of 12 repeats, 15 repeats and 16 repeats of a 38-bp repeat unit, respectively.

(2) MUC2-MS2 (Minisatellite 2)

100 normal persons were examined and, as a result, 65 alleles having a size of 390-4062 bp were found, which consisted of repeats of a 34-bp repeat unit.

(3) MUC2-MS3 (Minisatellite 3)

200 normal persons were examined and, as a result, four alleles having a size of 475-505 bp were found, which consisted of repeats of a 12-bp repeat unit.

(4) MUC2-MS4 (Minisatellite 4)

818 normal persons were examined and, as a result, six alleles having a size of 190-690 bp were found, which consisted of repeats of a 60-bp repeat unit.

(5) MUC2-MS6 (Minisatellite 6)

Figure 3:
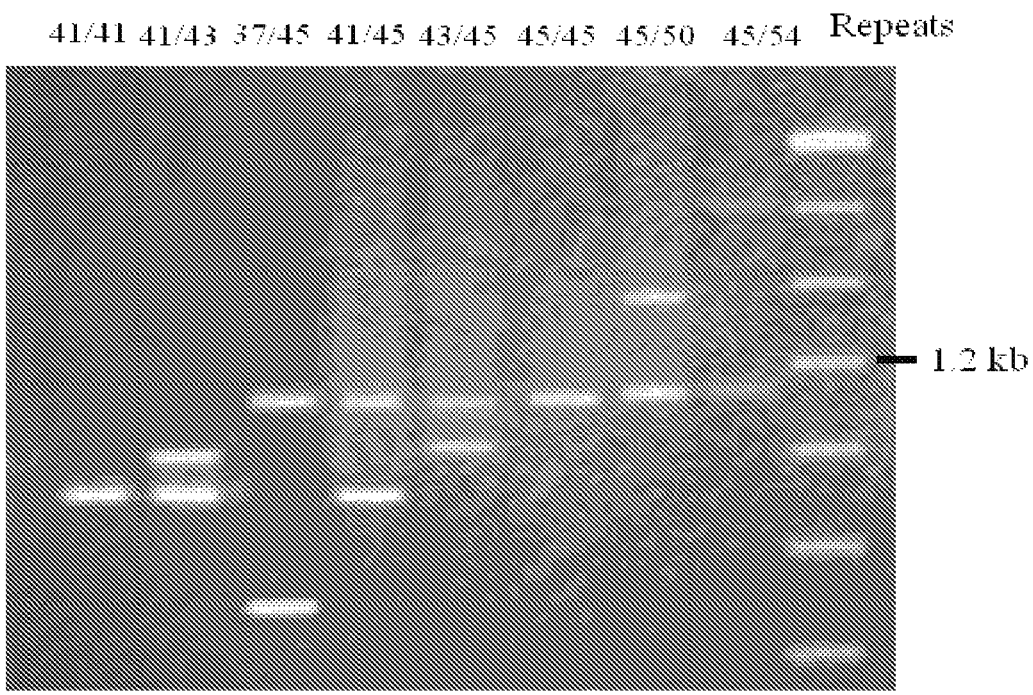
FIG. 3 is an electrophoresis photograph showing the polymorphism of MUC2-MS6.

731 normal persons were examined and, as a result, six alleles having a size of 983-1391 bp were found, which consisted of 37-54 repeats of a 24-bp repeat unit (see Table 3 and FIG. 3).

TABLE 3

Analysis of polymorphism of MUC2-MS6

| Repeats | Size (bp) | N = 1462 | Frequency |
|---|---|---|---|
| 37 | 983 | 1 | 0.001 |
| 40 | 1055 | | |
| 41 | 1079 | 81 | 0.055 |

TABLE 3-continued

Analysis of polymorphism of MUC2-MS6

| Repeats | Size (bp) | N = 1462 | Frequency |
|---|---|---|---|
| 42 | 1103 | | |
| 43 | 1127 | 7 | 0.005 |
| 44 | 1151 | | |
| 45 | 1175 | 1361 | 0.931 |
| 46 | 1199 | | |
| 47 | 1223 | | |
| 50 | 1295 | 1 | 0.001 |
| 54 | 1391 | 11 | 0.008 |

(6) MUC2-MS7 (Minisatellite 7)

Figure 4:
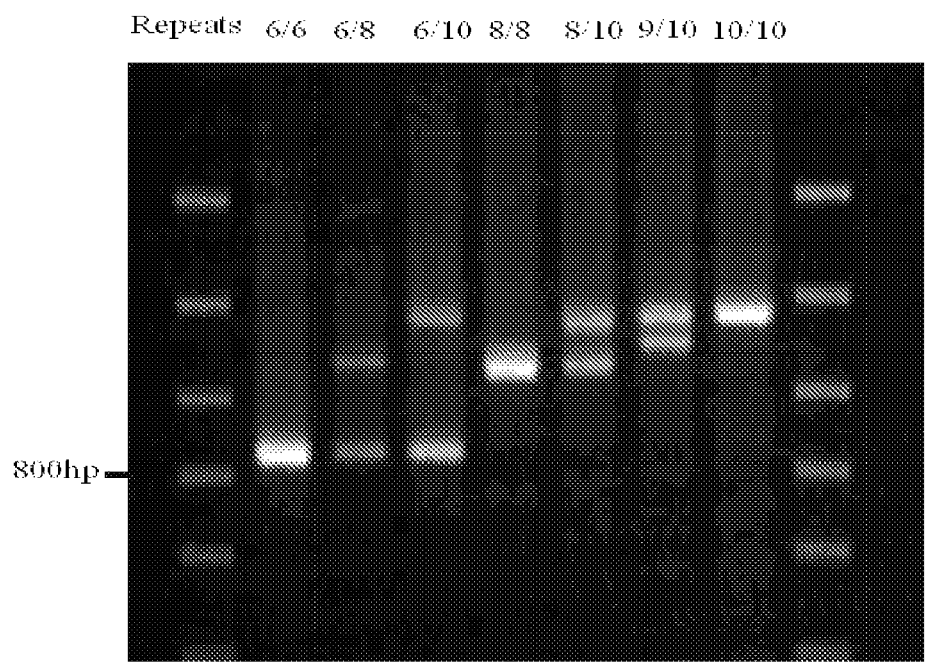
FIG. 4 is an electrophoresis photograph showing the polymorphism of MUC2-MS7.

767 normal persons were examined and, as a result, four alleles having a size of 416-600 bp were identified, which consisted of 6 repeats, 8 repeats, 9 repeats and 10 repeats of a 46-bp repeat unit, indicating that MUC2-MS7 showed polymorphism (see Table 4 and FIG. 4).

TABLE 4

Analysis of polymorphism of MUC2-MS7

| | | Total amounts | |
|---|---|---|---|
| Repeats | Size (bp) | N = 1490 | Frequency |
| 6 | 833 | 362 | 0.2430 |
| 8 | 925 | 292 | 0.1960 |
| 9 | 971 | 1 | 0.0007 |
| 10 | 1017 | 835 | 0.5603 |

Example 2

Genetic Inheritance of Polymorphic Minisatellites (MS) Through Meiosis

Genomic DNA was extracted from the blood of grandparents, parents and offspring and subjected to PCR in the same manner as in Example 1 to examine the allele patterns of MUC2-MS1, MUC2-MS3, MUC2-MS4, MUC2-MS6 and MUC2-MS7.

Figure 5:
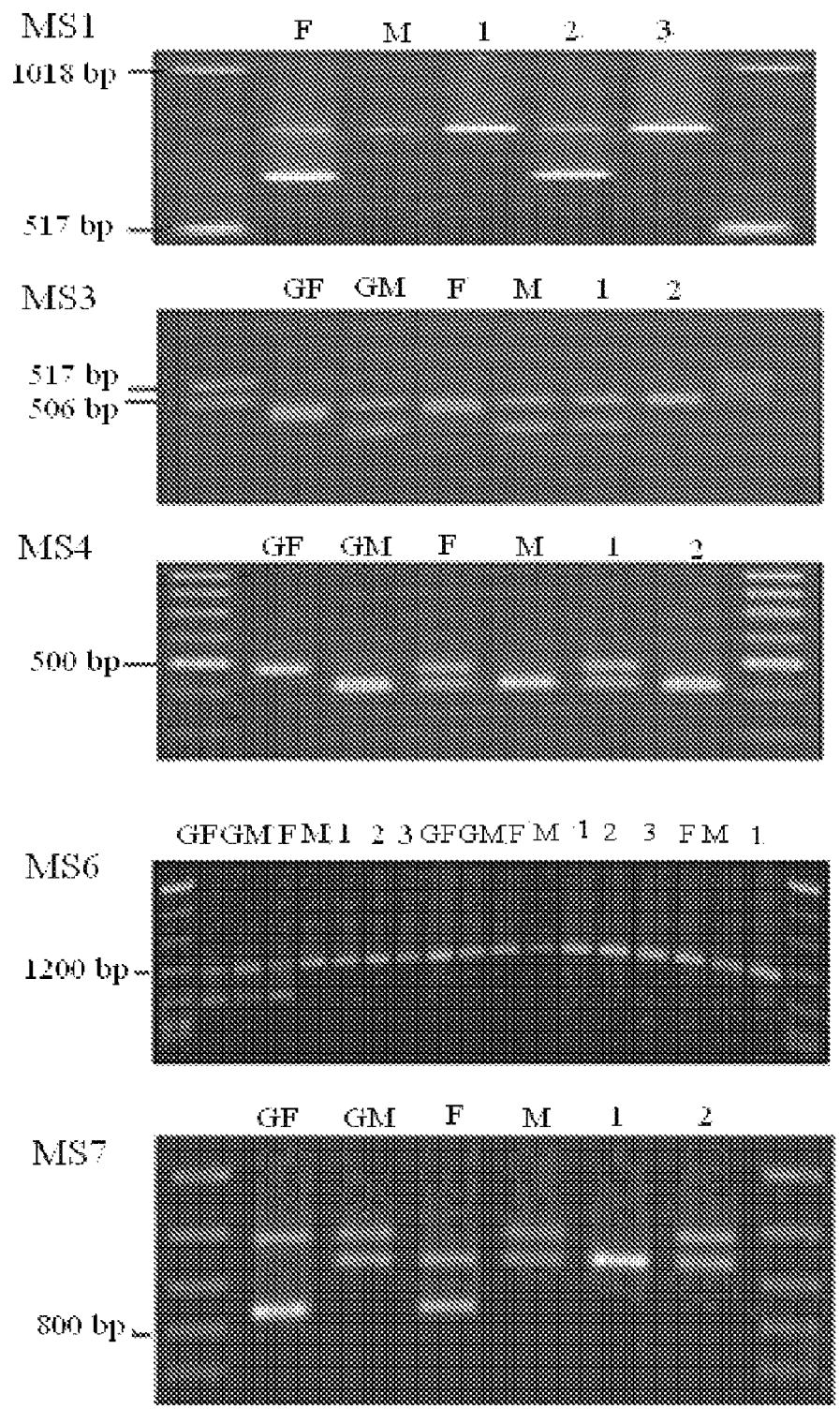
FIG. 5 is an electrophoresis photograph showing that MUC2-MS1, MUC2-MS3, MUC2-MS4, MUC2-MS6 and MUC2-MS7 are genetically inherited from parents to offspring.

As a result, it could be seen that MUC2-MS1, MUC2-MS3, MUC2-MS4, MUC2-MS6 and MUC2-MS7 were all genetically inherited from parents to offspring through meiosis (FIG. 5). This suggests that minisatellites in the MUC2 gene are inherited according to the Mendel's law and can be used as efficient markers for individual identification, parentage identification, kinship identification or medicolegal examination, and such DNA typing markers can be used to predict whether the same disease would occur in the same family.

Also, whether the MUC2 minisatellites have heterozygosity was measured and, as a result, MUC2-MS1, MUC2-MS2, MUC2-MS3, MUC2-MS4, MUC2-MS6 and MUC2-MS7 showed heterozygosity in the range of 0.125-0.977 (see Table 5). Particularly, MUC2-MS6 showed heterozygosity in gastric cancer patients and colon cancer patients, and MUC2-MS7 showed heterozygosity in rectal cancer patients (see Table 6).

TABLE 5

Heterozygosity of MUC2 minisatellites

| Minisatellite | Hetrozygosity | Analyzed control samples |
|---|---|---|
| MUC2-MS1 | 0.499 | 400 |
| MUC2-MS2 | 0.977 | 100 |
| MUC2-MS3 | 0.650 | 200 |
| MUC2-MS4 | 0.542 | 818 |
| MUC2-MS5 | 0 | 100 |
| MUC2-MS6 | 0.125 | 1029 |
| MUC2-MS7 | 0.585 | 1229 |
| MUC2-MS8 | 0 | 100 |

TABLE 6

Heterozygosity of MUC2-MS6 and MUC2-MS7 in normal persons and cancer patients

| Minisatellite | Case | Analyzed samples | Hetrozygosity | Relative ratio |
|---|---|---|---|---|
| MUC2-MS6 | Control | 1029 | 0.125 | 1 |
|  | Gastric cancer | 491 | 0.163 | 1.304 |
|  | Colon cancer | 207 | 0.094 | 0.752 |
|  | Rectal cancer | 272 | 0.163 | 1.304 |
| MUC2-MS7 | Control | 1229 | 0.585 | 1 |
|  | Gastric cancer | 486 | 0.583 | 0.997 |
|  | Colon cancer | 220 | 0.635 | 1.09 |
|  | Rectal cancer | 279 | 0.588 | 1.01 |

Example 3

Measurement of Correlation of MUC2-MS1 MUC2-MS3, MUC2-MS4, MUC2-MS6 and MUC2-MS7 Regions with Gastric Cancer The fact that the structural characteristics of tandem repeats (TR) are involved in the expression of genes was reported with respect to h-Ras. Thus, in order to examine the effects of the TR regions on the expression of the MUC2, genomic DNA was extracted from normal persons and gastric cancer patients and subjected to PCR in the same manner as in Example 1 to compare haplotype patterns between the normal persons and the gastric cancer patients.

(1) MUC2-MS1

400 normal persons and 400 gastric cancer patients were analyzed for the MUC2-MS1 region. In the case of the gastric cancer patients, two alleles having sizes of 644 bp and 796 bp were found, which consisted of 12 repeats and 16 repeats of a 38-bp repeat unit, respectively. In this region, no gastric cancer-specific allele appeared.

(2) MUC2-MS3

200 normal persons and 200 gastric cancer patients were analyzed for the MUC2-MS3 region. In the case of the gastric cancer patients, four alleles having a size of 475-505 bp were found, which consisted of 25.5 repeats, 26.5 repeats, 27.5 repeats and 28 repeats of a 12-bp repeat unit, respectively. In this region, no gastric cancer-specific allele appeared.

(3) MUC2-MS4

818 normal persons and 433 gastric cancer patients were analyzed for the MUC2-MS4 region. As a result, 6 alleles having a size of 190-690 bp were found, which consisted of 1 repeat, 3 repeats, 4 repeats, 5 repeats, 6 repeats and 10 repeats of a 60-bp repeat unit, respectively. In this region, no gastric cancer-specific allele appeared.

(4) MUC2-MS6

Figure 6:
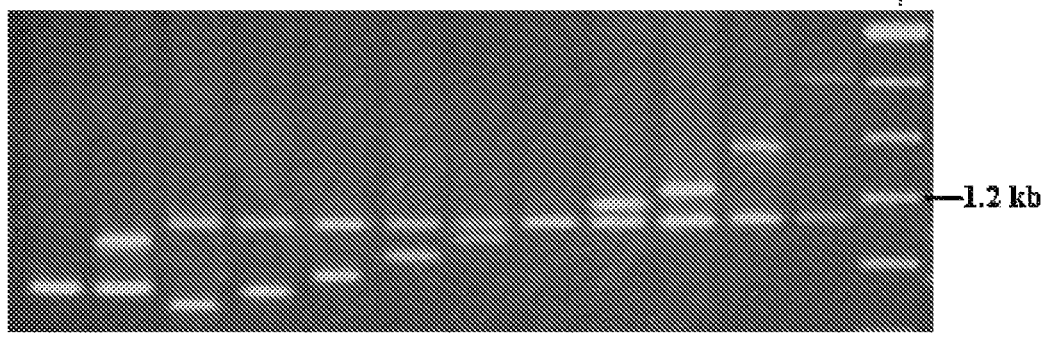
FIG. 6 is an electrophoresis photograph showing the gastric cancer-specific polymorphism of MUC2-MS6.

731 normal persons and 500 gastric cancer patients were analyzed for the MUC2-MS6 region. In the case of the gastric cancer patients, 10 alleles having a size of 1055-1391 bp were found, which consisted of 40 repeats, 41 repeats, 42 repeats, 43 repeats, 44 repeats, 45 repeats, 46 repeats, 47 repeats, 50 repeats and 54 repeats of a 24-bp repeat unit, respectively (see Table 7 and FIG. 6). Particularly, in the samples of the gastric cancer patients, gastric cancer-specific alleles consisting of 42 repeats, 44 repeats and 47 repeats, respectively, which did not appear in the normal persons, were found. This suggests that the rare alleles of MUC2-MS6 are related to gastric cancer.

TABLE 7

Analysis of gastric cancer-specific polymorphism of MUC2-MS6

|  |  | Normal persons |  | Gastric cancer patients |  |
|---|---|---|---|---|---|
| Repeat | Size (bp) | N = 1462 | Frequency | N = 1000 | Frequency |
| 37 | 983 | 1 | 0.001 |  |  |
| 40 | 1055 |  |  | 1 | 0.001 |
| 41 | 1079 | 81 | 0.055 | 54 | 0.054 |
| 42 | 1103 |  |  | 6 | 0.006 |
| 43 | 1127 | 7 | 0.055 | 16 | 0.016 |
| 44 | 1151 |  |  | 2 | 0.002 |
| 45 | 1175 | 1361 | 0.931 | 913 | 0.913 |
| 46 | 1199 |  |  | 1 | 0.001 |
| 47 | 1223 |  |  | 2 | 0.002 |
| 50 | 1295 | 1 | 0.001 | 4 | 0.004 |
| 54 | 1391 | 11 | 0.008 | 3 | 0.003 |

Alleles, the frequency of which is less than 1% of the number of normal individuals, are defined as rare alleles, and these rare alleles of MUC2-MS6 and their sensitivity to cancer development were analyzed (see Table 8). The resulting allele patterns were divided into a pattern C/C consisting only of common alleles, and a pattern R/- having at least one rare allele, and the divided patterns were compared to each other.

As a result, it was observed that the R/- pattern in the gastric cancer patients was about 2.5-fold higher than that in the normal persons. This suggests that, in the case of having the rare allele of MUC2-MS6, the sensitivity to gastric cancer is about 2.5-fold higher than that in normal persons, thus indicating that MUC2-MS6 is an important marker for examining the sensitivity to gastric cancer and can be used as an important material for predicting and diagnosing gastric cancer.

TABLE 8

Rare allele patterns of MUC2-MS6 in normal persons and gastric cancer patients

|  | Normal persons |  | Gastric cancer patients |  |
|---|---|---|---|---|
| Pattern | N | % | N | % |
| C/C | 711 | 97.26 | 467 | 93.40 |
| R/— | 20 | 2.74 | 33 | 6.60 |

C: common allele,
R: rare allele,
—: cancer specific allele (5) MUC2-MS7

Figure 7:
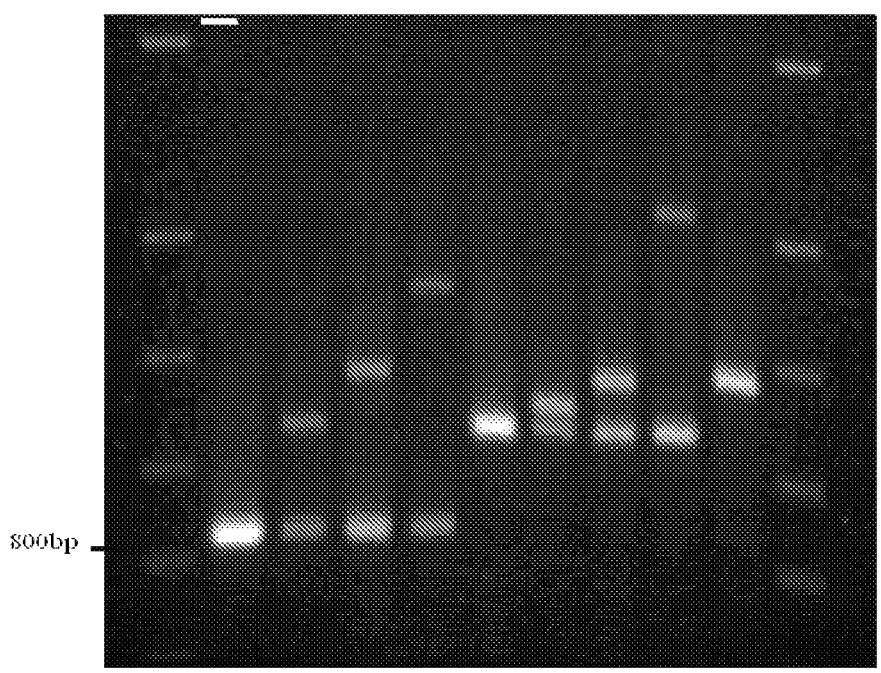
FIG. 7 is an electrophoresis photograph showing the gastric cancer-specific polymorphism of MUC2-MS7.

745 normal persons and 486 gastric cancer patients were analyzed for the MUC2-MS7 region. In the case of the gastric cancer patients, 6 alleles having a size of 833-1247 bp were identified, which consisted of 6 repeats, 8 repeats, 9 repeats, 10 repeats, 13 repeats and 15 repeats of a 46-bp repeat unit, respectively. Particularly, in the gastric cancer patients, gastric cancer-specific alleles consisting of 13 repeats and 15 repeats, respectively, which did not appear in the normal persons, were found (see Table 9 and FIG. 7). This suggests that, because the rare allele of MUC2-MS7 is related to gastric cancer, MUC2-MS7 can be used as a marker for predicting and diagnosing gastric cancer.

TABLE 9

Analysis of gastric cancer-specific polymorphism of MUC2-MS7

|  |  | Normal persons | | Gastric cancer patients | |
|---|---|---|---|---|---|
| Repeat | Size (bp) | N = 1490 | Frequency | N = 972 | Frequency |
| 6 | 833 | 362 | 0.2430 | 238 | 0.2449 |
| 8 | 925 | 292 | 0.1960 | 178 | 0.1831 |
| 9 | 971 | 1 | 0.0007 | 1 | 0.0010 |
| 10 | 1017 | 835 | 0.5604 | 553 | 0.5689 |
| 13 | 1155 | — | — | 1 | 0.0010 |
| 15 | 1247 | — | — | 1 | 0.0010 |

The rare allele of MUC2-MS7 and its sensitivity to cancer development were analyzed (Table 10). As a result, it was observed that the R/- patterns in the gastric cancer patients was about 7.5-fold higher than that in the normal persons. This suggests that, in the case of having the rare allele of MUC2-MS7, the sensitivity to gastric cancer is about 7.5-fold higher than that in normal persons.

TABLE 10

Rare allele patterns of MUC2-MS7 in normal persons and gastric cancer patients

|  | Normal persons | | Gastric cancer patients | |
|---|---|---|---|---|
| Pattern | N | % | N | % |
| C/C | 744 | 99.87 | 483 | 99.38 |
| R/— | 1 | 0.13 | 3 | 0.62 |

C: common allele,
R: rare allele,
—: cancer specific allele

Example 4

Sensitivity of Rare Alleles of MUC2-MS6 and MUC2-MS7 to Tumor Development

The frequencies of MUC2-MS6 and MUC2-MS7 in normal persons and tumor patients were measured. As a result, the frequency of rare alleles of MUC2-MS6 was 1.26% in normal persons, whereas it was 3.56% in gastric cancer patients. Also, the frequency of rare alleles of MUC2-MS7 was 0.08% in normal persons, whereas it was 0.54% in rectal cancer patients (Table 11). This suggests that the rare alleles of MUC2-MS6 are related to gastric cancer (OR, 2.89; 95% CI, 1.73-4.83; p=0.00002), and the rare alleles of MUC2-MS7 are related to rectal cancer (OR, 6.64; 95% CI, 1.11-39.82; p=1.016).

TABLE 11

Frequencies and the risk of tumor development of rare alleles of MUC2-MS6 and MUC2-MS7

| MUC2-MS6 | | Control | Gastric cancer | Colon cancer | Rectal cancer |
|---|---|---|---|---|---|
| Analyzed alleles (%) | | 2058 | 982 | 414 | 554 |
| Common alleles | 41 | 110 (5.73) | 50 (5.09) | 10 (2.42) | 30 (5.51) |
|  | 45 | 1922 (93.39) | 897 (91.34) | 394 (95.17) | 506 (91.34) |
|  | Total | 2032 (98.74) | 947 (96.44) | 506 (91.34) | 536 (98.53) |
| Rare alleles | 37 | 1 | 0 | 0 | 0 |
|  | 40 | 1 | 1 | 0 | 0 |
|  | 42 | 0 | 6 | 0 | 0 |
|  | 43 | 8 | 16 | 2 | 4 |
|  | 44 | 0 | 2 | 3 | 3 |
|  | 46 | 0 | 1 | 0 | 0 |
|  | 47 | 0 | 2 | 0 | 0 |
|  | 50 | 1 | 4 | 1 | 0 |
|  | 54 | 15 | 3 | 2 | 1 |
|  | 57 | 0 | 0 | 2 | 0 |
|  | 62 | 0 | 0 | 0 | 0 |
|  | Total | 26 (1.26) | 35 (3.56) | 10 (2.42) | 8 (1.47) |
| OR (95% CI) | | 1.00 | 2.89 (1.73~4.83) | 1.93 (0.93~4.04) | 1.17 (0.53~2.59) |
| P | | — | 0.00002* | 0.07 | 0.71 |
| MUC2-MS7 | | Control | Gastric cancer | Colon cancer | Rectal cancer |
| Analyzed alleles (%) | | 2458 | 972 | 440 | 558 |
| Common alleles | 6 | 594 (24.17) | 238 (24.49) | 110 (25.00) | 142 (25.45) |
|  | 8 | 472 (19.20) | 178 (18.31) | 83 (18.86) | 107 (19.18) |
|  | 10 | 1390 (56.55) | 553 (56.89) | 246 (55.90) | 306 (54.84) |
|  | Total | 2456 (99.92) | 969 (99.69) | 439 (99.77) | 555 (99.46) |

TABLE 11-continued

Frequencies and the risk of tumor development of rare alleles of MUC2-MS6 and MUC2-MS7

| Rare alleles | 7 | 0 | 0 | 0 | 1 |
|---|---|---|---|---|---|
| | 9 | 2 | 1 | 1 | 2 |
| | 13 | 0 | 1 | 0 | 0 |
| | 15 | 0 | 1 | 0 | 0 |
| Total | | 2 (0.08) | 3 (0.31) | 1 (0.23) | 3 (0.54) |
| OR (95% CI) | | 1.00 | 3.80 (0.63~22.79) | 2.80 (0.25~30.92) | 6.64 (1.11~39.82) |
| P | | — | 0.12 | 0.38 | 0.016* |

*Statistically significant (p < 0.02)

The rare alleles of MUC2-MS6 were found in gastric cancer patients (4 rare alleles) and colon cancer patients (3 rare alleles), and the rare alleles of MUC2-MS7 were found in gastric cancer patients (2 rare alleles) and rectal cancer patients (1 rare allele). Such results were statistically analyzed and, as a result, in the case of having at least one rare allele of MUC2-MS6, the relative risk of gastric cancer development was 1.70-4.84 (p=0.00004) in a 95% confidence interval, and the relative risk of colon cancer development was 0.93-4.13 (p=0.00002) in a 95% confidence interval. Also, in the case of having at least one rare allele of MUC2-MS7, the relative risk of rectal cancer development was 1.11-40.10 (p=0.017) in a 95% confidence interval (see Table 12). This suggests that the rare alleles of MUC2-MS6 are not related to rectal cancer, but rather are related to gastric cancer and colon cancer, and the rare alleles of MUC2-MS7 are related to rectal cancer.

old were analyzed. As a result, the frequency of rare alleles of MUC2-MS6 was 2.68 (CI, 1.23-5.85; p=0.01) in the patients more than 50 years old, whereas it was 3.38 (CI, 1.51~7.56; p=0.0017) in the patients less than 50 years old. Also, the frequency of rare alleles of MUC2-MS6 in colon cancer patients was 1.79 (CI, 0.66-4.90; p=0.25) for the patients more than 50 years old, whereas it was 3.41 (CI, 0.95-12.21; p=0.046) for the patients less than 50 years old. This suggests that, as age decreases, the relationship of the rare alleles of MUC2-MS6 with gastric cancer and colon cancer is increased.

Moreover, the frequencies of rare alleles of MUC2-MS7 in rectal cancer patients more than 50 years old and rectal cancer patients less than 50 years old were analyzed. As a result, the frequency of rare alleles of MUC2-MS7 in the patients more than 50 years old was 2.49 (CI, 0.15-39.97; p=0.51), whereas

TABLE 12

Relationship of tumors with rare alleles of MUC2-MS6 and MUC2-MS7

| MUC2-MS6 (%) | Total case | C/C | C/R | + R/R | OR (95% CI) | P |
|---|---|---|---|---|---|---|
| Control | 1029 | 1003 (97.47%) | 26 | 26 (2.53%) | 1.00 | — |
| Gastric cancer | 491 | 457 (93.08%) | 33 + 1 | 34 (6.92%) | 2.87 (1.70~4.84) | 0.00004* |
| Colon cancer | 207 | 197 (95.17%) | 10 | 10 (4.83%) | 1.96 (0.93~4.13) | 0.00002 |
| Rectal cancer | 272 | 264 (97.06%) | 8 | 8 (2.94%) | 1.17 (0.52~2.61) | 0.70 |

| MUC2-MS7 (%) | Total case | C/C | C/R | + R/R | OR (95% CI) | P |
|---|---|---|---|---|---|---|
| Control | 1229 | 1227 (99.84%) | 2 | 2 (0.16%) | 1.00 | — |
| Gastric cancer | 486 | 483 (99.38%) | 3 | 3 (0.62%) | 3.81 (0.63~22.88) | 0.12 |
| Colon cancer | 220 | 219 (99.54%) | 1 | 1 (0.46%) | 2.80 (0.25~31.03) | 0.38 |
| Rectal cancer | 279 | 276 (98.92%) | 3 | 3 (1.08%) | 6.67 (1.11~40.10) | 0.017* |

C/C, common alleles only;
C/R, one rare allele/one common allele;
R/R, two rare alleles
*Statistically significant (p < 0.02)

Table 13 below shows the frequency of alleles of MUC2-MS6 and MUC2-MS7 according to age. The frequencies of rare alleles of MUC2-MS6 in gastric cancer patients more than 50 years old and gastric cancer patients less than 50 years it was 25.85 (CI, 2.31-289.8; p=$1.05E^{-16}$) in the patients less than 50 year old. This suggests that, as age decreases, the relationship of rectal cancer with the rare alleles of MUC2-MS7 is increased.

TABLE 13

Frequencies of rare alleles of MUC2-MS6 and MUC2-MS7 according to age

| Age | Control | Gastric cancer | OR(95% CI) | P | Colon cancer | OR(95% CI) | P | Rectal cancer | OR(95% CI) | P |
|---|---|---|---|---|---|---|---|---|---|---|
| MUC2-MS6: frequency of rare alleles (%) | | | | | | | | | | |
| <50 | 17/654 (2.60) | 10/121 (7.43) | 3.38 (1.51~7.56) | 0.0017* | 3/36 (8.33) | 3.41 (0.95~12.21) | 0.046* | 2/54 (3.70) | 1.44 (0.32~6.41) | 0.63 |
| ≧50 | 9/357 (2.52) | 24/370 (5.82) | 2.68 (1.23~5.85) | 0.01* | 7/158 (4.43) | 1.79 (0.66~4.90) | 0.25 | 6/217 (2.76) | 1.10 (0.39~3.13) | 0.86 |
| MUC2-MS7: frequency of rare alleles (%) | | | | | | | | | | |
| <50 | 1/673 (0.15) | 1/106 (0.94) | 6.4 (0.40~103.1) | 0.13 | 0/37 (0.00) | — | — | 2/54 (3.70) | 25.85 (2.31~289.8) | 1.05E−16* |
| ≧50 | 1/556 (0.18) | 2/366 (0.55) | 3.05 (0.28~33.75) | 0.34 | 1/160 (0.63) | 3.49 (0.22~56.12) | 0.07 | 1/224 (0.45) | 2.49 (0.15~39.97) | 0.51 |

*Statistically significant (p < 0.05)

Example 5

Measurement of Instability of Polymorphic Minisatellites of MUC2 in Tumor Tissues Because the MUC2 gene contains a high density of minisatellites playing a role in the instability of chromosomes, the rearrangements of alleles of polymorphic minisattelites of MUC2-MS2, MUC2-MS6 and MUC2-MS7 were compared with each other. For this purpose, DNA was extracted from the blood and tumor tissues of 28 gastric cancer patients and subjected to PCR in the same manner as in Example 1 to compare the number of repeats. As a result, the polymorphic minisatellites of MUC2-MS6 had the same number of repeats (FIG. 8b), whereas, in the case of MUC2-MS2, there was a deletion or loss of four heterozygosities in DNA obtained from tumor tissue (FIG. 8a), and in the case of MUC2-MS7, there was a deletion or loss of two heterozygosities (FIG. 8c).

Figure 8:
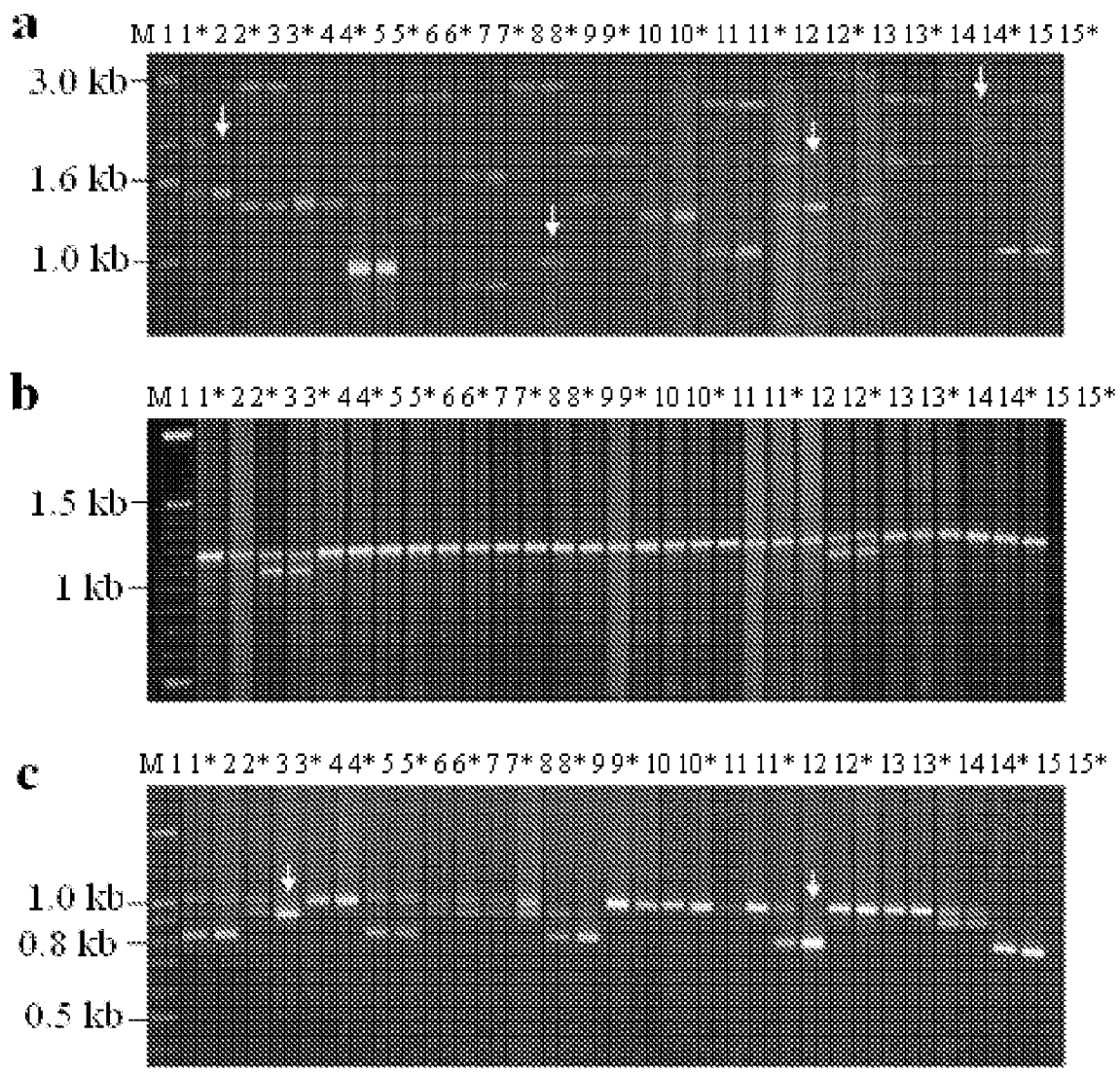
FIG. 8 shows measurement results for the instability of MUC2 minisatellites (a: MUC2-MS2; b: MUC2-MS6; c: MUC2-MS7) in blood and tumor tissues extracted from a gastric cancer patient.

The repeat number of rearrangement in gastric cancer patient was 14.3% for MUC2-MS2 and 7.1% for MUC2-MS7, and in one patient, rearrangements were observed in both MUC2-MS2 and MUC2-MS7 (FIG. 8a and 8c; line 11 and 11*). This suggests that the rearrangements are not related to the rare alleles of MUC2, the extent of tumors, and medical histories.

Example 6

Measurement of Relationship of hTERT-VNTR 2-2 Region with Prostate Cancer

The human telomerase reverse transcriptase (hTERT) gene includes four minisatellites (VNTR 2-1, VNTR 2-2, VNTR 6-1 and VNTR 6-2) (Table 14).

TABLE 14

Tandem repeats present in hTERT gene

| VNTR | Consensus sequences | Location | Size (bp) | SEQ ID NO: |
|---|---|---|---|---|
| VNTR 2-1 | GAGTGAGGCGTGGTCCCCGGGTGTCCCTG TCACGTGCAGGGT | Intron 2 | 42 | 25 |
| VNTR 2-2 | C(T)G(T)GTGAGCTGGATGTGC(T)GGT GTCC(T)GGATGGTGCAGGTCC(T)GGGG TGAGGTCGCCAGGCCCTG | Intron 2 | 61 | 26 |
| VNTR 6-1 | GTGGGATTGGTTTTCATGTGCGGGGTAGG TGGGGATCT | Intron 6 | 38 | 27 |
| VNTR 6-2 | GGGGTCTGATGTGTGGTGACTGTGGATGG CGGTCGT | Intron 6 | 36 | 28 |

The polymorphisms of the minisatellites were analyzed by PCR. The base sequences of primers used in the PCR analysis are shown in Table 15 below.

TABLE 15

Primers used for detection of polymorphisms

| Polymorphisms | Primer | Sequence | SEQ ID NO: |
|---|---|---|---|
| VNTR 2-1 | VNTR 2-1 F | GCTGCGTCTTGCGTGACTGG | 29 |
|  | VNTR 2-1 R | TACCCAGGCAATGGGCAACC | 30 |
| VNTR 2-2 | VNTR 2-2 F | TGGGAGCATCACTCACAGGA | 31 |
|  | VNTR 2-2 R | GGAACACAGCCAACCCCTTA | 32 |
| VNTR 6-1 | VNTR 6-1 F | GTGACGTTGCTTCTGTGCCTCCTT | 33 |
|  | VNTR 6-1 R | CGACCCCAGAGTGGAAGAAACAGA | 34 |
| VNTR 6-2 | VNTR 6-2 F | ACTCTTCTCCTGCCTGTGCTGTGG | 35 |
|  | VNTR 6-2 R | GTTTCTTCCGATCAGGACGTGTGG | 36 |

In previous studies, the present inventors found that VNTR 6-1 and 6-2 are effective in diagnosing telomerase-related diseases, because they have chromosomal rearrangements different from those of normal tissues (Korean Patent Registration No. 10-0431285). In the present invention, VNTR 2-2 was found to be particularly useful for diagnosing prostate cancer.

The frequencies of rare alleles of the hTERT-VNTR (human telomerase reverse transcriptase-variable number of tandem repeats) 2-2 region in normal males and prostate cancer patients were examined. As a result, the frequencies were 0.51% and 2.14%, which are more than 4-fold different from each other. Such results were statistically analyzed and, as a result, in the case of having the rare allele of hTERT-VNTR 2-2, the risk (odds ratio, OR; risk ratio) of prostate cancer development was increased by 8.32 times at a 95% confidence interval (p=0.017, statistically very significant) (Table 16). This suggests that the hTERT-VNTR 2-2 region can be used to predict and diagnose prostate cancer.

TABLE 16

Frequency of rare alleles of hTERT VNTR 2-2

| hTERT-2-2nd | Total number | C/C | C/R | OR (95% CI) | p |
|---|---|---|---|---|---|
| No. of control (%) | 736 | 735 (99.73%) | 1 (0.27%) | 1.00 (reference) | |
| No. of female (%) | 346 | 346 (100%) | 0 | | |
| No. of breast cancer (%) | 517 | 515 (99.61%) | 2 (0.39%) | 2.85 (0.26~31.56) | 0.37 |
| Mo. of prostate cancer (%) | 374 | 366 (97.86%) | 8 (2.14%) | 16.07 (2.0~128.9) | 0.0004 |
| No. of male (%) | 390 | 389 (99.49%) | 1 (0.51%) | 1.00 (reference) | |
| No. prostate cancer (%) | 374 | 366 (97.86%) | 8 (2.14%) | 8.32 (1.0~66.8) | 0.017 |

Figure 9:
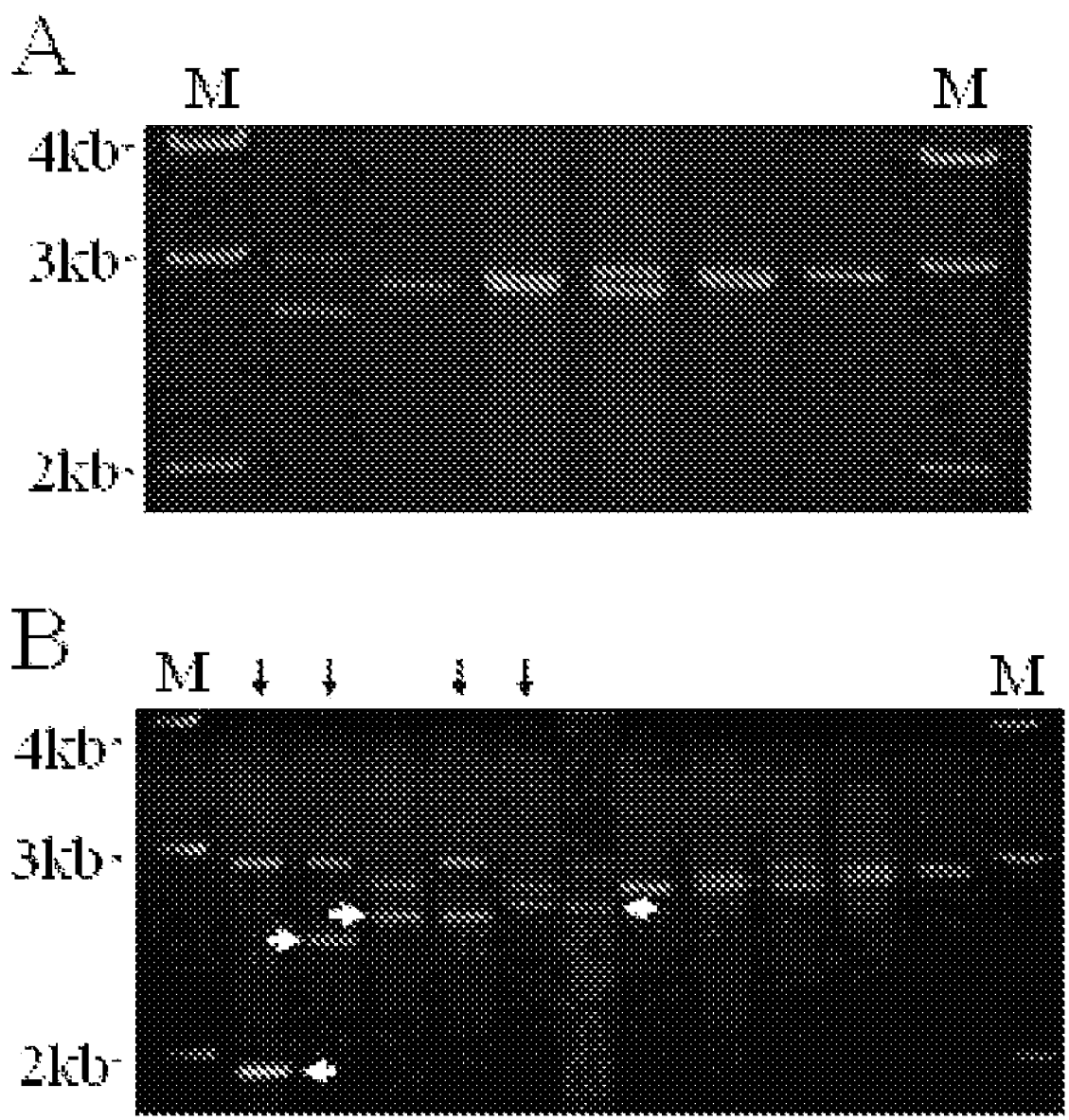
FIG. 9 is an electrophoresis photograph showing a prostate cancer-specific polymorphism of hTERT-VNTR 2-2. Specifically.

In addition, for the hTERT VNTR 2-2 region, genomic DNA was extracted from 390 normal persons and 374 prostate cancer patients and subjected to PCR with the primers shown in Table 15 to compare haplotype patterns between the normal persons and the prostate cancer patients. As a result, in the prostate cancer patients, 7 alleles were found, which consisted of 28 repeats, 37 repeats, 39 repeats, 40 repeats, 42 repeats, 43 repeats and 44 repeats of a 61-bp repeat unit, respectively (see Table 17 and FIG. 9). Particularly, in the samples of the prostate cancer patients, prostate cancer-specific alleles consisting of 28 repeats, 37 repeats and 40 repeats, respectively, which did not appear in the normal persons, were found. This suggests that the rare allele of hTERT VNTR 2-2 is related to prostate cancer.

TABLE 17

Analysis of prostate cancer-specific polymorphism of hTERT VNTR 2-2

| | | Normal persons | | Prostate cancer patients | |
|---|---|---|---|---|---|
| Repeat | Size (bp) | N = 780 | Frequency | N = 748 | Frequency |
| 28 | 1934 | | | 1 | 0.0013 |
| 37 | 2483 | | | 1 | 0.0013 |
| 39 | 2605 | 1 | 0.0013 | 4 | 0.0054 |
| 40 | 2666 | | | 2 | 0.0027 |
| 42 | 2788 | 287 | 0.3679 | 266 | 0.3556 |
| 43 | 2849 | 14 | 0.0179 | 14 | 0.0187 |
| 44 | 2910 | 478 | 0.6128 | 460 | 0.6150 |

INDUSTRIAL APPLICABILITY

As described in detail above, because the polymorphic minisatellites MUC2-MS6 and MUC2-MS7 according to the present invention are inherited through meiosis according to Mendelian genetics, DNA typing of the polymorphic minisatellites MUC2-MS6 and MUC2-MS7 can effectively achieve the parentage identification, kinship identification or medicolegal examination. Also, because the polymorphic minisatellites MUC2-MS6, MUC2-MS7 and hTERT VNTR 2-2 are found in cancer-specific alleles appearing in patients having tumors such as gastric cancer, colon cancer, rectal cancer and prostate cancer, the sensitivity to cancer can be diagnosed by amplifying the MUC2-MS6, MUC2-MS7 and hTERT VNTR 2-2 regions and comparing the frequency of rare alleles of the regions to that of normal persons.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

What is claimed is:

1. An isolated polymorphic minisatellite for predicting and diagnosing a tumor selected from the group consisting of gastric cancer, colon cancer and rectal cancer, the polymorphic minisatellite consisting of SEQ ID NO: 6 (MUC2-minisatellite6, MUC2-MS6) or SEQ ID NO: 7 (MUC2-minisatellite7, MUC2-MS7).

2. A set of primers for detecting SEQ ID NO: 6 (MUC2-MS6) of claim 1, the primers consisting of SEQ ID NO: 19 and SEQ ID NO: 20, respectively.

3. A set of primers for detecting SEQ ID NO: 7 (MUC2-MS7) of claim 1, the primers consisting of SEQ ID NO: 21 and SEQ ID NO: 22, respectively.

4. A DNA typing kit for detecting a polymorphic minisatellite consisting of SEQ ID NO: 6 (MUC2-MS6) the DNA typing kit comprising the primer set of claim 2.

5. A kit for diagnosing a tumor selected from the group consisting of gastric cancer, colon cancer and rectal cancer, the kit comprising the primer set of claim 2, DNA polymerase and dNTPs (dGTP, dCTP, dATP and dTTP).

6. An isolated polymorphic minisatellite hTERT-VNTR (human telomerase reverse transcriptase-variable number of tandem repeats) 2-2 for predicting and diagnosing prostate cancer, the polymorphic minisatellite hTERT-VNTR 2-2 consisting of SEQ ID NO: 26.

7. A kit for diagnosing prostate cancer which comprises a set of primers for detecting polymorphic minisatellite hTERT-VNTR 2-2, DNA polymerase and dNTPs (dGTP, dCTP, dATP and dTTP), the primers consisting of SEQ ID NO: 31 and SEQ ID NO: 32, respectively.

8. A DNA typing kit for detecting a polymorphic minisatellite consisting of SEQ ID NO: 7 (MUC2-MS7), the DNA typing kit comprising the primer set of claim 3.

9. A kit for diagnosing a tumor selected from the group consisting of gastric cancer, colon cancer and rectal cancer, the kit comprising the primer set of claim 3, DNA polymerase and dNTPs (dGTP, dCTP, dATP and dTTP).

* * * * *